(12) United States Patent
Oh et al.

(10) Patent No.: US 11,202,714 B2
(45) Date of Patent: Dec. 21, 2021

(54) BASEPLATE TRIAL HOLDING APPARATUS AND KNEE JOINT IMPLANT SURGICAL INSTRUMENT SET INCLUDING THE SAME

(71) Applicant: CORENTEC CO., LTD., Chungcheongnam-do (KR)

(72) Inventors: Seung-Hun Oh, Seoul (KR); Chan-Eol Kim, Seoul (KR); Seok-Joo Kim, Seoul (KR); Oui-Sik Yoo, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 35 days.

(21) Appl. No.: 16/494,623

(22) PCT Filed: Mar. 19, 2018

(86) PCT No.: PCT/KR2018/003176
§ 371 (c)(1),
(2) Date: Sep. 16, 2019

(87) PCT Pub. No.: WO2018/174495
PCT Pub. Date: Sep. 27, 2018

(65) Prior Publication Data
US 2020/0085592 A1 Mar. 19, 2020

(30) Foreign Application Priority Data
Mar. 24, 2017 (KR) ........................ 10-2017-0037830

(51) Int. Cl.
*A61F 2/46* (2006.01)
*A61F 2/38* (2006.01)
(Continued)

(52) U.S. Cl.
CPC ............ *A61F 2/4684* (2013.01); *A61B 17/56* (2013.01); *A61F 2/461* (2013.01); *A61B 17/1675* (2013.01);
(Continued)

(58) Field of Classification Search
CPC ............ A61B 17/1604; A61B 17/1764; A61B 17/1735; A61B 17/1675; A61B 17/56;
(Continued)

(56) References Cited

U.S. PATENT DOCUMENTS

| 5,356,414 | A | 10/1994 | Cohen | |
|---|---|---|---|---|
| 7,001,394 | B2 * | 2/2006 | Gundlapalli | ........ A61B 17/1764 606/86 R |
| 8,491,587 | B2 * | 7/2013 | McGovern | ........... A61B 17/155 606/86 R |
| 8,979,847 | B2 * | 3/2015 | Belcher | ................ A61B 17/157 606/79 |

FOREIGN PATENT DOCUMENTS

| JP | 4316176 B2 | 8/2009 |
|---|---|---|
| KR | 10-2006-0135633 A | 12/2006 |

(Continued)

OTHER PUBLICATIONS

International Search Report dated Aug. 13, 2018, issued in PCT Application No. PCT/KR2018/003176 filed Mar. 19, 2018.
(Continued)

*Primary Examiner* — Marcela I. Shirsat
(74) *Attorney, Agent, or Firm* — Workman Nydegger

(57) ABSTRACT

A baseplate trial holding apparatus which holds a baseplate trial disposed in a proximal tibia during total knee arthroplasty or revision total knee arthroplasty, and includes a keel location setting part for setting an insertion location of a keel punch, and a knee joint implant surgical instrument set including the same.

19 Claims, 16 Drawing Sheets

(51) Int. Cl.
  *A61B 17/17*  (2006.01)
  *A61B 17/16*  (2006.01)
  *A61B 17/56*  (2006.01)

(52) U.S. Cl.
  CPC ........... *A61B 17/1764* (2013.01); *A61F 2/389* (2013.01); *A61F 2002/4687* (2013.01)

(58) Field of Classification Search
  CPC ........... A61B 17/157; A61B 2017/0046; A61F 2/4684; A61F 2/461; A61F 2/389; A61F 2002/30476; A61F 2002/30492; A61F 2002/30604; A61F 2002/4625; A61F 2002/4628; A61F 2002/4687; A61F 2/46
  USPC ..................... 606/88; 623/20.32, 20.15, 20.4
  See application file for complete search history.

(56) References Cited

FOREIGN PATENT DOCUMENTS

| | | |
|---|---|---|
| KR | 10-2008-0010224 A | 1/2008 |
| KR | 10-0822471 B1 | 4/2008 |

OTHER PUBLICATIONS

Written Opinion dated Aug. 13, 2018, issued in PCT Application No. PCT/KR2018/003176 filed Mar. 19, 2018.

\* cited by examiner

BASEPLATE TRIAL HOLDING APPARATUS AND KNEE JOINT IMPLANT SURGICAL INSTRUMENT SET INCLUDING THE SAME

BACKGROUND OF THE INVENTION

1. Field of the Invention

The present disclosure relates to a baseplate trial holding apparatus and a knee joint implant surgical instrument set including the same, and more particularly to a baseplate trial holding apparatus which holds a baseplate trial disposed in a proximal tibia during total knee arthroplasty or revision total knee arthroplasty, and includes a keel location setting part for setting an insertion location of a keel punch, and a knee joint implant surgical instrument set including the same.

2. Description of the Prior Art

In total knee arthroplasty or revision total knee arthroplasty, a coupling location of a tibia implant is set before coupling of the tibia implant and a baseplate trial is temporarily fixed to a tibia to secure a space for embedding an implant in the tibia.

A baseplate trial holding apparatus is used to grip a baseplate trial, set a coupling location on a tibia, and perform drilling, reaming, offsetting, and the like, and referring to FIG. 1, a conventional baseplate trial holding apparatus 10 includes a body 11 and a handle 13, and the body 11 overlapping the baseplate trial 20 generally has a cylindrical shape. This is for seating a drill guide, an offset bush guide, a reamer guide, and the like in the body 11 to perform processes, such as drilling, offsetting, reaming, and the like. However, the cylindrical body 11 has a form in which a keel punch including a stem portion and a wing portion cannot pass through the body 11, and for an operation of the keel punch, the baseplate trial holding apparatus 10 has to be separated and a separate keel punch guide has to be coupled to the baseplate trial 20 to be used.

Meanwhile, because the body 11 of the baseplate trial holding apparatus 10 has to have a relatively large inner diameter when it is necessary to secure a wide space for embedding an implant in the tibia as in the case in which the state of the tibia is not good during revision total knee arthroplasty or a primary surgery (total knee arthroplasty) even though the body 11 is intended to be configured such that the keel punch may be inserted into the body 11, the inner diameter of the body 11 becomes larger than the outer diameter of the stem portion of the keel punch so that it is impossible to stably realize a keel punch guide.

In this situation, as the keel punch can be guided regardless of the inner diameter of the body 11 of the baseplate trial holding apparatus 10 in total knee arthroplasty or revision total knee arthroplasty, development of a technology for omitting use of separate guide equipment for an operation of the keel punch has been required for improving of the efficiency of a surgery.

SUMMARY OF THE INVENTION

The present disclosure has been made in an effort to solve the above-described problems of the related art, and provides a baseplate trial holding apparatus that can perform the function of a guide for setting an insertion location of a keel punch in a state of being coupled to a baseplate trial.

The present disclosure also provides a baseplate trial holding apparatus that can guide a keel punch by preventing horizontal movement of a keel punch by a guide slit having a shape corresponding to curving of a keel wing portion of the keel punch.

The present disclosure also provides a baseplate trial holding apparatus that can set the center of a keel punch during insertion of the keel punch by a guide slit that guides insertion of a keel wing portion of the keel punch.

The present disclosure also provides a baseplate trial holding apparatus that can have a form for rearward fixing and forward fixing, and thus precisely guide a keel punch through a keel location fixing part for determining an insertion limit of the keel punch during forward fixing.

The present disclosure also provides a baseplate trial holding apparatus that can guide a keel stem portion of a keel punch through a keel location fixing part.

The present disclosure also provides a baseplate trial holding apparatus that can be firmly coupled to a baseplate trial through a locking unit press-fitted with a coupling recess formed in the baseplate trial.

The present disclosure also provides a baseplate trial holding apparatus that can facilitate easy insertion of a pin for fixing a baseplate trial to a tibia in a state in which the baseplate trial holding apparatus is coupled to the baseplate trial.

The present disclosure also provides a baseplate trial holding apparatus that can function to guide a keel punch in a state in which the baseplate trial holding apparatus is coupled to a baseplate trial and in which an offset bush guide, a drill guide, and a reamer guide are seated to be used.

The present disclosure also provides a baseplate trial holding apparatus that can perform rotation-stop type indexing of an offset bush guide through an indexing unit.

The present disclosure also provides a baseplate trial holding apparatus that can secure a precise coupling location with a baseplate trial through a boss insertion hole, through which a boss protruding from a proximal surface of a baseplate trial may be inserted.

The present disclosure also provides a baseplate trial holding apparatus, and a knee joint implant surgical instrument set including a baseplate trial coupled to the baseplate trial holding apparatus.

The present disclosure also provides a knee joint implant surgical instrument set including a baseplate trial having two or more sizes and a keel punch having two or more widths of keel wing portions corresponding to the sizes, wherein the baseplate trial holding apparatus allows passing of the keel wing portions of all widths, and the baseplate trial passes only the keel wing portion of the keel punch having the width of the keel wing portion corresponding to the size thereof.

The present disclosure also provides a knee joint implant surgical instrument set including a drill guide, an offset bush guide, and a reamer guide that can be stably seated in the baseplate trial holding apparatus.

The present disclosure is realized by the embodiments having the following configurations to achieve the objectives.

According to an aspect of the present disclosure, a baseplate trial holding apparatus is an apparatus for holding a baseplate trial disposed in a proximal tibia during total knee arthroplasty or revision total knee arthroplasty and may include a keel location setting part configured to set an insertion location of a keel punch.

The keel location setting part may include a central through portion, through which a keel stem portion of the keel punch passes, and a guide slit configured to guide insertion of a keel wing portion of the keel punch.

A guide slit may include a guide corresponding to curving of the keel wing portion of the keel punch.

The guide may be formed to protrude or be recessed complementarily with the curving of the keel wing portion of the keel punch.

The guide slit may be opened to the outside of the central through portion to communicate with the central through portion.

A pair of guide slits may be formed outside the central through portion to be symmetrical to each other, and may be formed while defining at an angle of less than 180° with reference to the center of the central through portion.

The baseplate trial holding apparatus may further include a keel location fixing part configured to determine an insertion limit of the keel punch.

The keel location fixing part may include a stopper formed in a form of being able to be fixed forwards and fixed rearwards, and brought into a state of being introduced into the central through portion during forward fixing to cause an upper end of a keel of the keel punch to be hooked when the keel punch is inserted.

The stopper assists guiding of the keel punch as an end of the stopper, which is introduced into the central through portion, to contact the keel stem portion of the keel punch while having a shape that is complementary with the keel stem portion of the keel punch during the forward fixing.

The central through portion may define a seating space partitioned by an inner wall thereof such that any one of a drill guide, an offset bush guide, and a reamer guide is seated in the seating space.

The central through portion may be formed such that the drill guide, the offset bush guide, and the reamer guide are inserted and seated not to move horizontally.

The central through portion may have a cylindrical shape, the baseplate trial holding apparatus may further include an indexing unit protruding from the inner wall of the central through portion in a form of being able to be pressed by an external force and restored by elasticity, and when the offset bush guide is seated in the central through portion while having indexing grooves formed on an outer surface of the offset bush guide, which contacts the inner wall of the central through portion, rotation-stop type indexing of the offset bush guide may be allowed.

The baseplate trial holding apparatus may further include a plate fixing part for coupling with the baseplate trial.

The plate fixing part may include a boss insertion hole formed such that a boss protruding from a proximal surface of the baseplate trial is inserted into the boss insertion hole when being coupled to the baseplate trial.

The plate fixing part further may include a locking unit press-fitted with a coupling recess formed in the baseplate trial for coupling with the baseplate trial when being coupled to the baseplate trial.

The baseplate trial holding apparatus may further include a pin insertion part formed to communicate with a pin hole formed in the baseplate trial to secure an insertion space of a pin that fixes the baseplate trial to a tibia.

According to another aspect of the present disclosure, a knee joint implant surgical instrument set includes the baseplate trial holding apparatus, and a baseplate trial coupled to the baseplate trial holding apparatus.

The baseplate trial may include a window passing through the baseplate trial to expose a proximal surface of a tibia and communicating with the keel location setting part of the baseplate trial holding apparatus.

The window may include a window central portion, through which a keel stem portion of the keel punch passes, and a window slit opened to opposite sides of the window central portion to communicate with the window central portion and through which the keel wing portion of the keel punch passes.

The length of the window slit may be smaller than or equal to the length of the guide slit.

The knee joint implant surgical instrument set may further include one or more of a drill guide having a form of being able to be seated in the central through portion of the baseplate trial holding apparatus, a offset bush guide having a form of being able to be seated in the central through portion of the baseplate trial holding apparatus, and a reamer guide having a form of being able to be seated in the central through portion of the baseplate trial holding apparatus.

Each of the drill guide, the offset bush guide, and the reamer guide may include a seating portion seated in the central through portion while contacting the inner wall of the central through portion to be inserted into the central through portion so as not to move horizontally when being seated in the central through portion.

The present disclosure has the following effects through the above-described configurations.

The present disclosure can provide a baseplate trial holding apparatus that can perform the function of a guide for setting an insertion location of a keel punch in a state of being coupled to a baseplate trial.

The present disclosure can provide a baseplate trial holding apparatus that can guide a keel punch by preventing horizontal movement of a keel punch by a guide slit having a shape corresponding to curving of a keel wing portion of the keel punch.

The present disclosure can provide a baseplate trial holding apparatus that can set the center of a keel punch during insertion of the keel punch by a guide slit that guides insertion of a keel wing portion of the keel punch.

The present disclosure can provide a baseplate trial holding apparatus that can have a form for rearward fixing and forward fixing, and thus precisely guide a keel punch through a keel location fixing part for determining an insertion limit of the keel punch during forward fixing.

The present disclosure can provide a baseplate trial holding apparatus that can guide a keel stem portion of a keel punch through a keel location fixing part.

The present disclosure can provide a baseplate trial holding apparatus that can be firmly coupled to a baseplate trial through a locking unit press-fitted with a coupling recess formed in the baseplate trial.

The present disclosure can provide a baseplate trial holding apparatus that can facilitate easy insertion of a pin for fixing a baseplate trial to a tibia in a state in which the baseplate trial holding apparatus is coupled to a baseplate trial.

The present disclosure can provide a baseplate trial holding apparatus that can function to guide a keel punch in a state in which the baseplate trial holding apparatus is coupled to a baseplate trial and in which an offset bush guide, a drill guide, and a reamer guide are seated to be used.

The present disclosure can provide a baseplate trial holding apparatus that can perform rotation-stop type indexing of an offset bush guide through an indexing unit.

The present disclosure can provide a baseplate trial holding apparatus that can secure a precise coupling location with a baseplate trial through a boss insertion hole, through which a boss protruding from a proximal surface of a baseplate trial may be inserted.

The present disclosure can provide a baseplate trial holding apparatus, and a knee joint implant surgical instrument set including a baseplate trial coupled to the baseplate trial holding apparatus.

The present disclosure can provide a knee joint implant surgical instrument set including a baseplate trial having two or more sizes and a keel punch having two or more widths of keel wing portions corresponding to the sizes, wherein the baseplate trial holding apparatus allows passing of the keel wing portions of all widths, and the baseplate trial passes only the keel wing portion of the keel punch having the width of the keel wing portion corresponding to the size thereof.

The present disclosure can provide a knee joint implant surgical instrument set including a drill guide, an offset bush guide, and a reamer guide that can be stably seated in the baseplate trial holding apparatus.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, a baseplate trial holding apparatus and a knee joint implant surgical instrument set including the same according to the present disclosure will be described in detail with reference to the accompanying drawings. All the terms of the specification are the same as the general meanings of the terms, which are understood by an ordinary person in the art to which the present disclosure pertains, and if the terms used in the specification do not agree with the general meanings of the terms, their meanings follow the definitions used in the specification. Further, a detailed description of the known functions and configurations that may make the essence of the present disclosure unclear will be omitted.

First, the baseplate trial holding apparatus 100 of the present disclosure will be described.

Referring to FIGS. 2 to 16, the baseplate trial holding apparatus 100 according to the embodiment of the present disclosure is an apparatus for holding a baseplate trial 200 disposed in a proximal tibia during total knee arthroplasty or revision total knee arthroplasty, and includes a keel location setting part 110 that sets an insertion location of a keel punch 300.

Because it is a basic premise that the baseplate trial holding apparatus 100 has a form of being folded with the baseplate trial 200 while covering the baseplate trial 200 and is coupled to the baseplate trial 200 to hold the baseplate trial 200, it is necessary to briefly discuss the baseplate trial 200 prior to discussing the elements of the baseplate trial holding apparatus 100.

Figure 1:
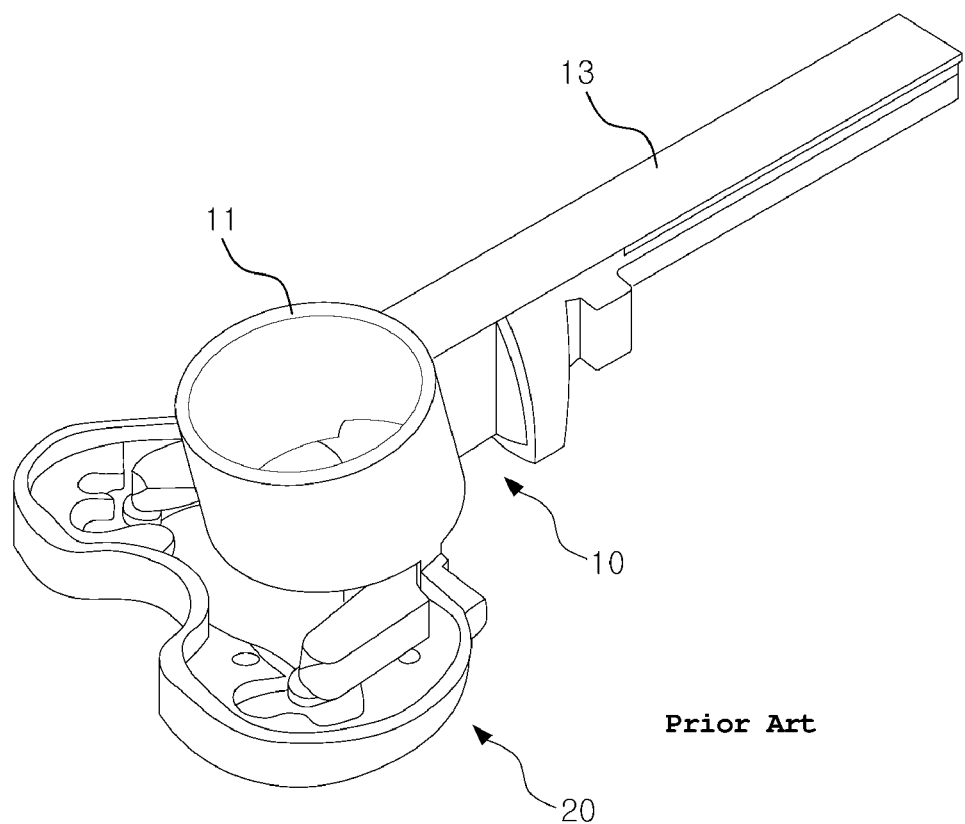
FIG. 1 is a perspective view of an embodiment of a conventional baseplate trial holding apparatus.
Figure 2:
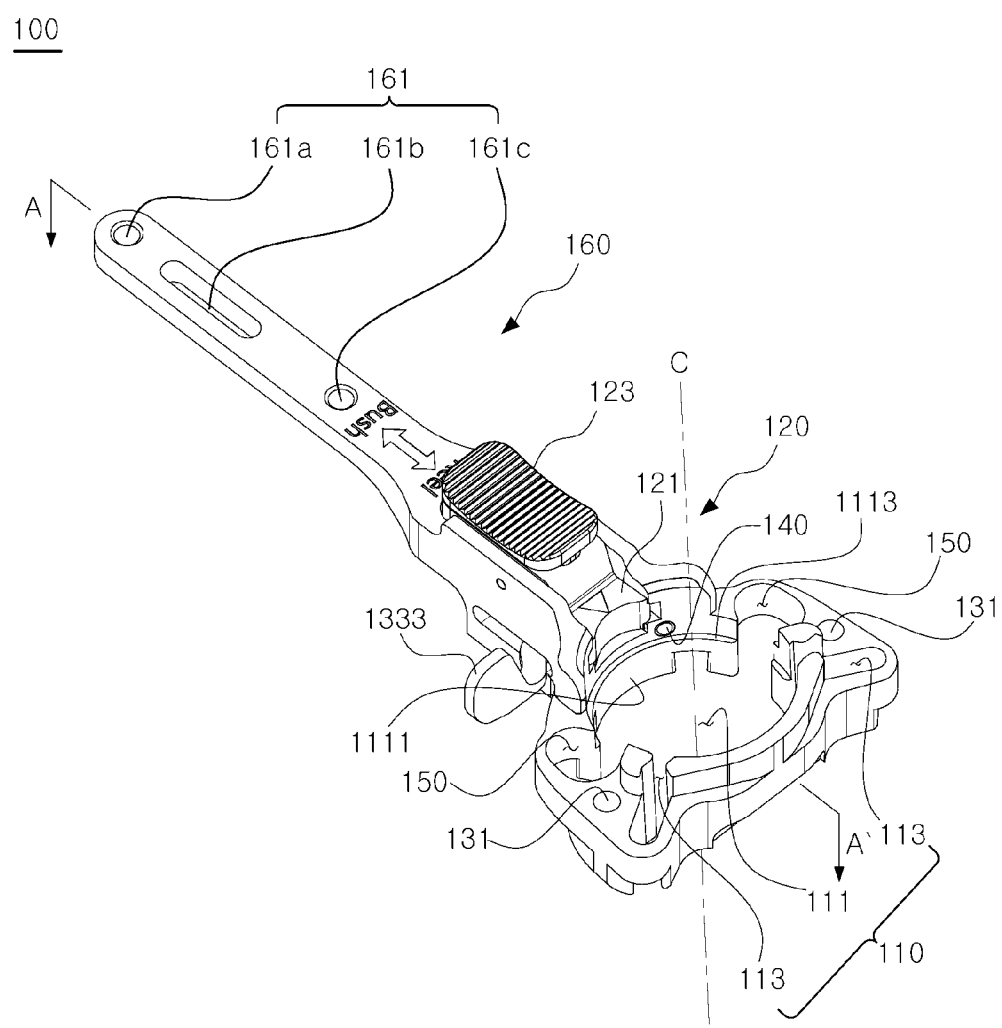
FIGS. 2 and 3 are a top perspective view and a bottom perspective view of a baseplate trial holding apparatus according to an embodiment of the present disclosure.
Figure 3:
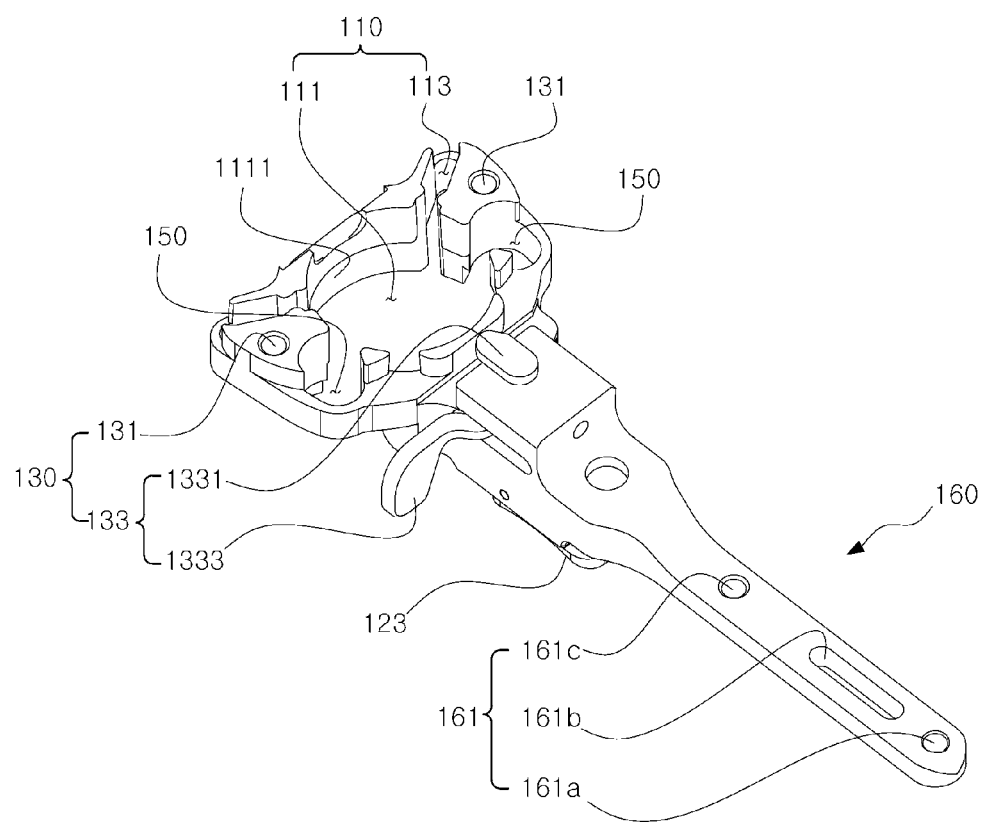
Figure 4:
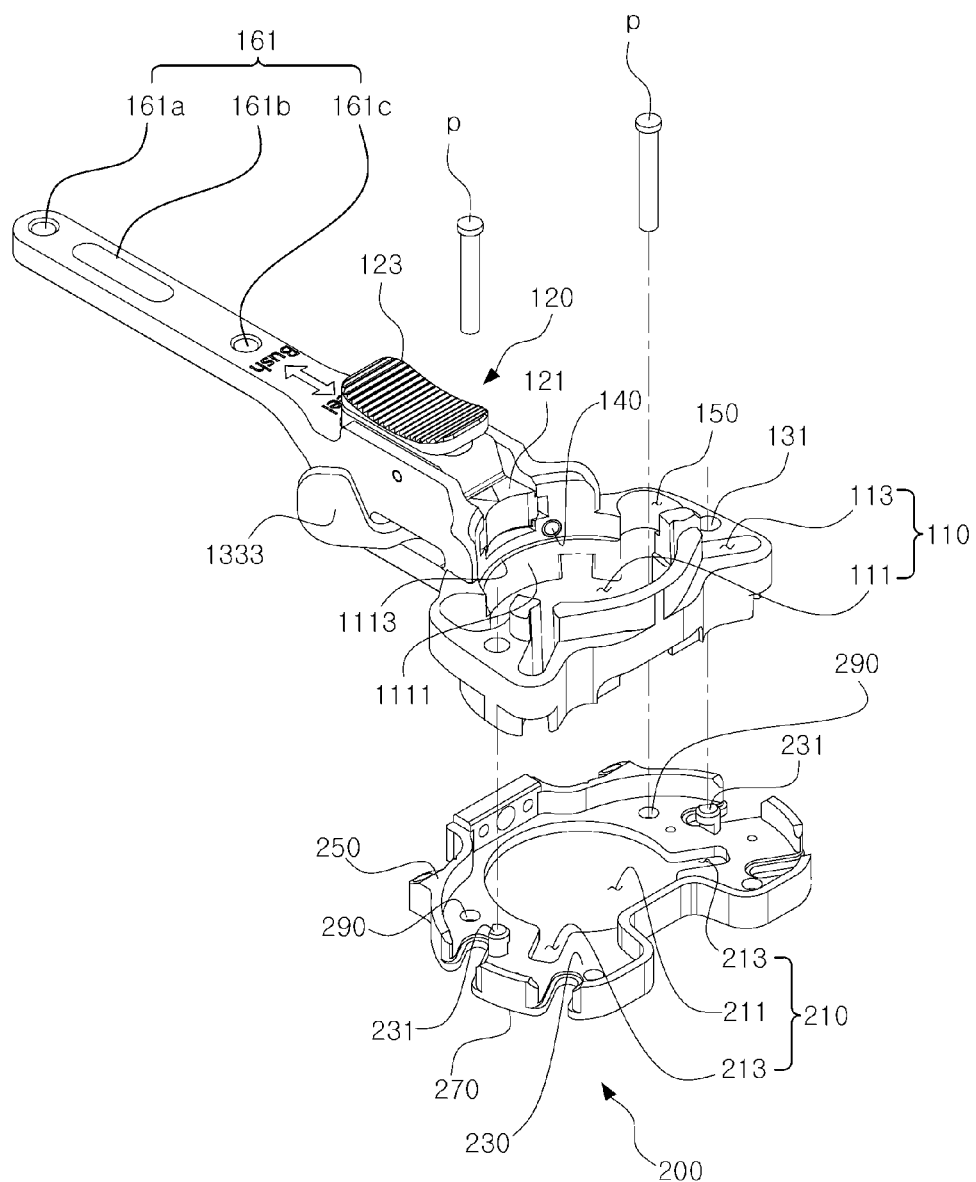
FIGS. 4 and 5 are a top perspective view and a bottom perspective view of a coupling state of the baseplate trial holding apparatus and a baseplate trial according to the embodiment of the present disclosure.
Figure 5:
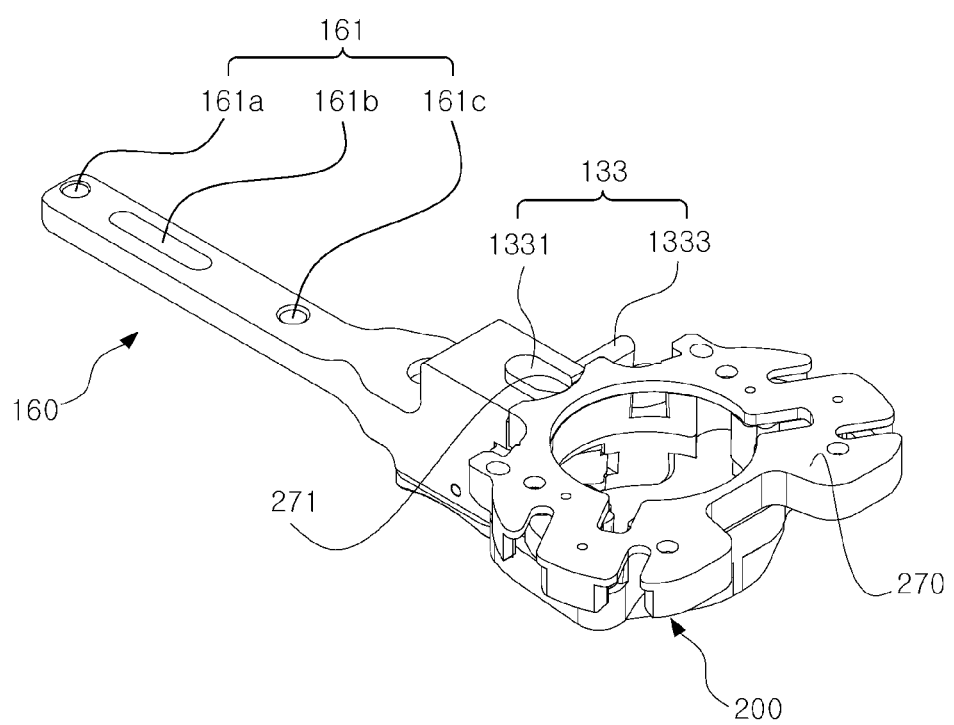

As can be identified through FIGS. 4 and 5, the baseplate trial 200 is a member which is used after being temporarily coupled to the tibia to perform an operation, such as setting of a coupling location of a tibia implant, drilling and reaming, or offsetting before a tibia implant is coupled to the tibia during the total knee arthroplasty or the revision total knee arthroplasty, and disposed in the cut proximal tibia to be used and includes a window 210, a proximal surface 230, a side wall 250, a distal surface 270, and a pin hole 290. The window 210 is a part which is disposed on the tibia proximal surface to expose the tibia, and includes a window central portion 211 that vertically passes through a central portion of the baseplate trial 200, and a window slit 213 that is opened on opposite sides of the window central portion 211 to communicate with the window central portion 211.

Hereinafter, a detailed configuration of the baseplate trial holding apparatus 100 will be described.

The baseplate trial holding apparatus 100 has a form in which an outskirt shape of a portion thereof, which is seated on the proximal surface 230 of the baseplate trial 200, may be inserted into a space defined by the side wall 250 protruding from an edge of the baseplate trial 200 in a proximal direction, and realizes a stable holding state while being folded on the baseplate trial 200. The baseplate trial holding apparatus 100 includes, in addition to the keel location setting part 110, a keel location fixing part 120, a plate fixing part 130, an indexing unit 140, a pin insertion part 150, and a handle 160.

The keel location setting part 110 is a part for setting an insertion location of the keel punch 300, and is formed to be vertically punched such that the keel punch 300 may pass through the keel location setting part 110. The keel location setting part 110 includes a central through portion 111 and a guide slit 113.

The central through portion 111 is a portion that communicates with the window 210 formed in the baseplate trial 200, and has a cylindrical shape. For example, a keel stem portion 311 of the keel punch 300 for forming a keel cavity in the interior of the tibia may be inserted through the central through portion 111 and the window 210.

The central through portion 111 defines a seating space partitioned by an inner wall 1111. As a result, as can be identified through FIGS. 12 to 16, an offset bush guide 400, a drill guide 500, a reamer guide 600, and the like may be seated in the central through portion 111. In detail, a seating step 1113 protruding from the inner wall 1111 is seated while seating portions 410, 510, and 610 of the offset bush guide 400, the drill guide 500, and the reamer guide 600 are hooked by the seating step 1113, and the central through portion 111 has a shape corresponding to the seating portions 410, 510, and 610, and restricts horizontal movements of the offset bush guide 400, the drill guide 500, and the reamer guide 600 when the offset bush guide 400, the drill guide 500, and the reamer guide 600 are seated.

Because the baseplate trial holding apparatus 100 not only functions as the keel punch guide 300 but also functions as a seating portion for the offset bush guide 400, the drill guide 500, and the reamer guide 600 due to the central through portion 111 in a state in which the baseplate trial holding apparatus 100 is coupled to the baseplate trial 200, a surgical process can be shortened.

The guide slit 113 is a portion that is opened to the outside of the central through portion 111 and communicates with the central through portion 111. The guide slit 113 communicates with the window slit 213 of the window 210. Through the guide slit 113, the baseplate trial holding apparatus 100 of the present disclosure can guide the keel punch 300 in a state in which the baseplate trial holding apparatus 100 is coupled to the baseplate trial 200.

Because a portion corresponding to the central through portion 111 has a cylindrical shape, of which all edges are blocked, a keel wing portion cannot be inserted according to the conventional baseplate trial holding apparatus, a separate keel punch guide has to be used after the baseplate trial holding apparatus is removed in order to secure an embedding space for the implant in the tibia by using the keel punch, but the present disclosure solves the inconvenience.

Figure 10:
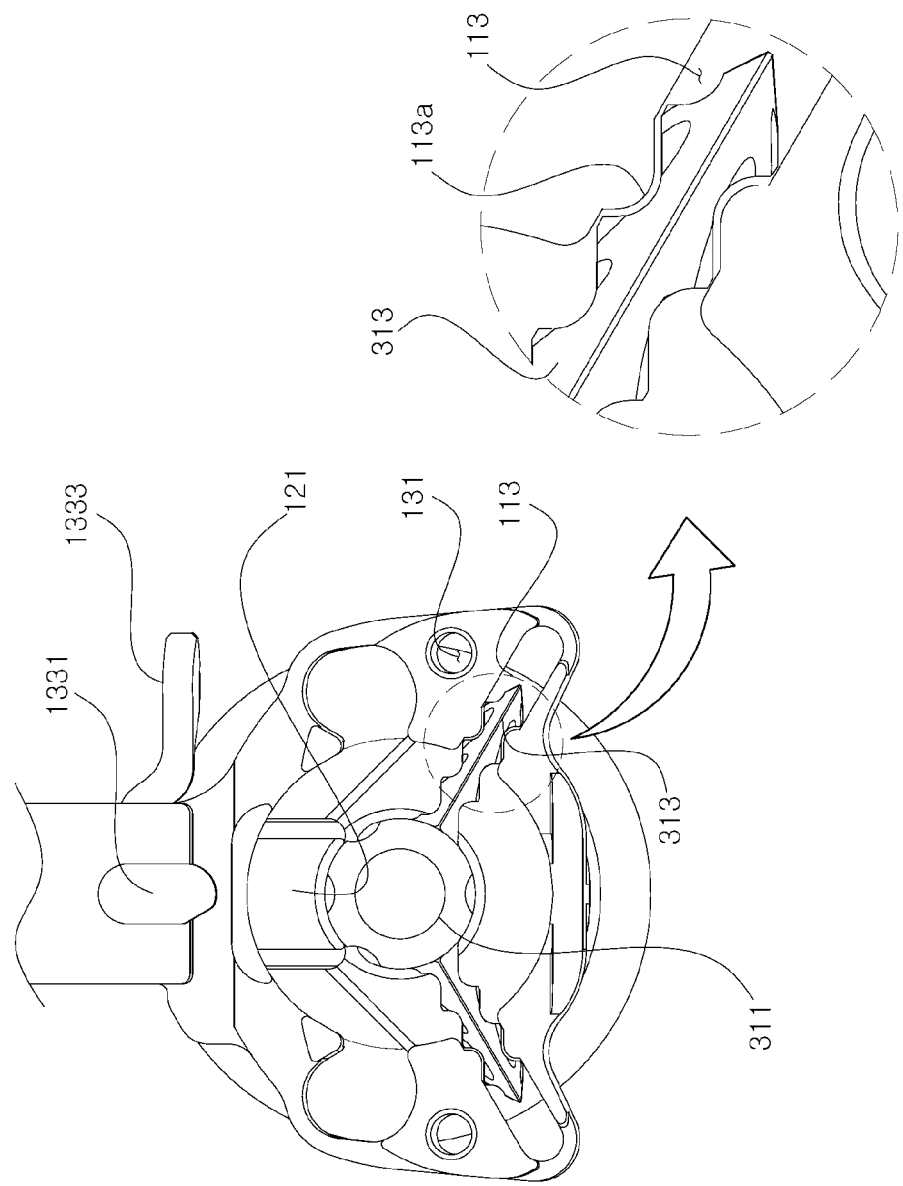
FIG. 10 is a bottom view of a state in which the keel punch is guided in the baseplate trial holding apparatus according to the embodiment of the present disclosure.

As illustrated in FIG. 10, the guide slit 113 includes a guide 113a corresponding to curving of the keel wing portion 313 of the keel punch 300. The guide 113a has a shape that protrudes or is recessed complementarily with the keel wing portion 313 of the keel punch 300, and the insertion of the keel punch 300 can be stably guided by restricting the horizontal movement of the keel punch 300 when the keel punch 300 is inserted.

That is, because the inner diameter of the central through portion 111 is larger than the outer diameter of the keel stem portion 311 of the keel punch 300 so that the guide 113a precisely guides the keel wing portions 313 on the opposite sides of the keel stem portion 311 of the keel punch 300 even when the keel stem portion 311 of the keel punch 300 is not precisely guided by the central through portion 111, the keel punch 300 can be precisely guided regardless of the inner diameter of the central through portion 111.

Accordingly, according to the present disclosure, even when the baseplate trial holding apparatus 100 is applied to a case in which a wider keel cavity has to be secured for embedding an implant in the tibia, for example, a case in which the state of the tibia is not good during revision total knee arthroplasty or a primary surgery (knee joint arthroplasty), the keel punch can be guided through the baseplate trial holding apparatus 100 even when the window central portion 211 of the baseplate trial 200 and the central through portion 111 of the baseplate trail holding apparatus 100 have relatively large diameters.

Figure 11:
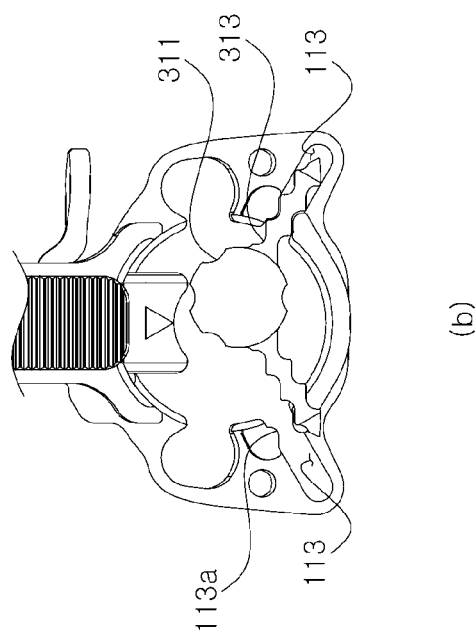
FIG. 11 is a conceptual view of a state in which the center of the keel punch is set in the baseplate trial holding apparatus according to the embodiment of the present disclosure.
Figure 11:
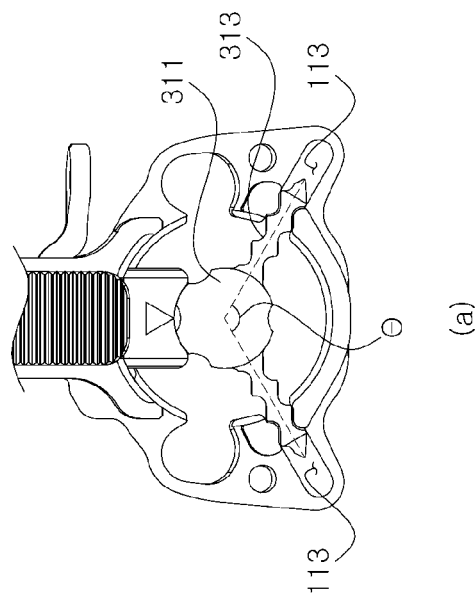

Further, the guide slit 113 is opened to the outside of the central through portion 111 and communicates with the central through portion 111. In more detail, a pair of guide slits 113 are symmetrically formed outside the central through portion 111, and as illustrated in FIG. 11, define an angle θ of less than 180° with reference to the center of the central through portion 111. Accordingly, when the keel punch 300 is inserted in a form in which the center (c of FIG. 2) of the central through portion 111 and the center (c' of FIG. 8) of the keel punch 300 coincide with each other, the keel stem portion 311 and the keel wing portion 313 of the keel punch 300 can be inserted as illustrated in a of FIG. 11. However, as illustrated in FIG. 11B, when the keel punch 300 is inserted such that the center (c of FIG. 2) of the central through portion 111 and the center (c' of FIG. 8) of the keel punch 300 do not coincide with each other, the keel wing portion 313 on one side of the keel punch 300 cannot be inserted into the guide slit 113 on the one side (the center (c of FIG. 2) of the central through portion 111 and the center (c' of FIG. 8) of the keel punch 300 mean the center in the insertion direction of the surgical instrument, and may be vertical or may be inclined at a predetermined angle). In the principle, the center of the keel punch 300 can be aligned through the guide slit 113.

The keel location fixing part 120 is a part that functions to determine an insertion limit of the keel punch 300. As described above, according to the present disclosure because the baseplate trial holding apparatus 100 is applied to a case in which a wide space for embedding an implant has to be secured in the tibia, as in an example in which the state of the tibia is not good during revision total knee arthroplasty or a primary surgery (total knee arthroplasty) so that the guide slit 113 can precisely guide the keel wing portion 313 of the keel punch 300 even when the window 210 of the baseplate trial 200 or the central through portion 111 of the baseplate trial holding apparatus 100 has a relatively large diameter, the keel punch can be guided through the baseplate trial holding apparatus 100. Then, a configuration for restricting the insertion degree of the keel punch 300 is necessary, and the keel location fixing part 120 performs the function.

Figure 6:
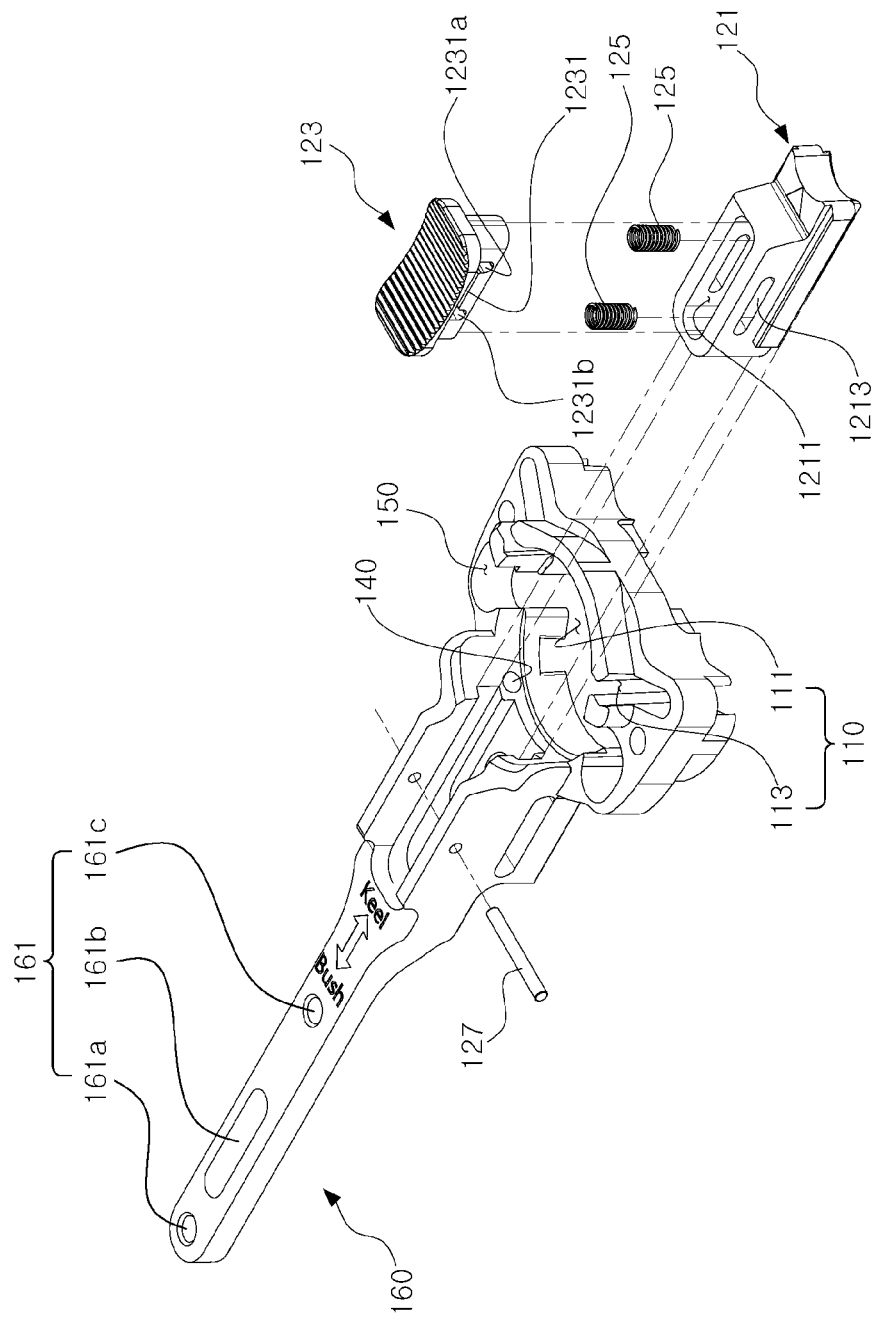
FIG. 6 is an exploded perspective view of the baseplate trial holding apparatus according to the embodiment of the present disclosure.
Figure 7:
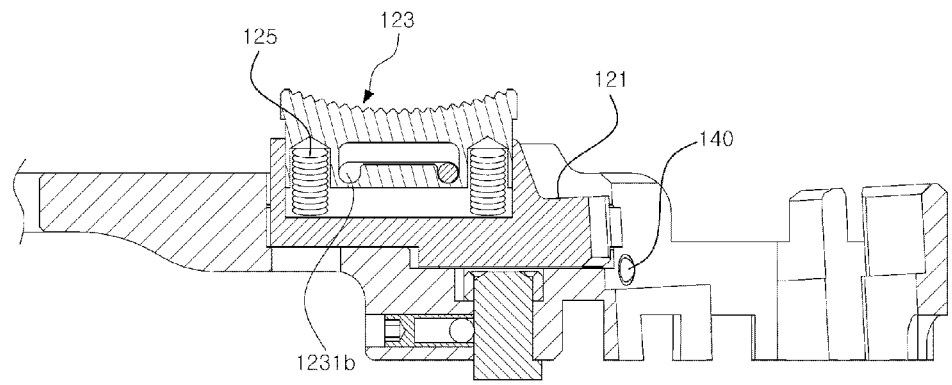
FIG. 7 is a cross-sectional view taken along section A-A' of FIG. 2.
Figure 7:
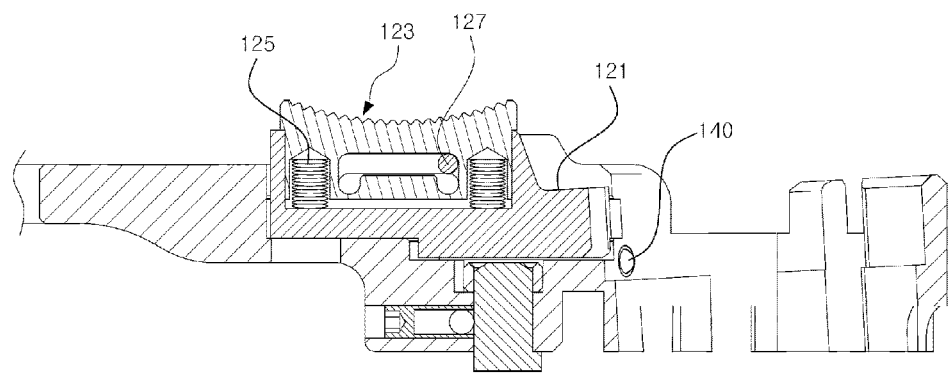
Figure 7:
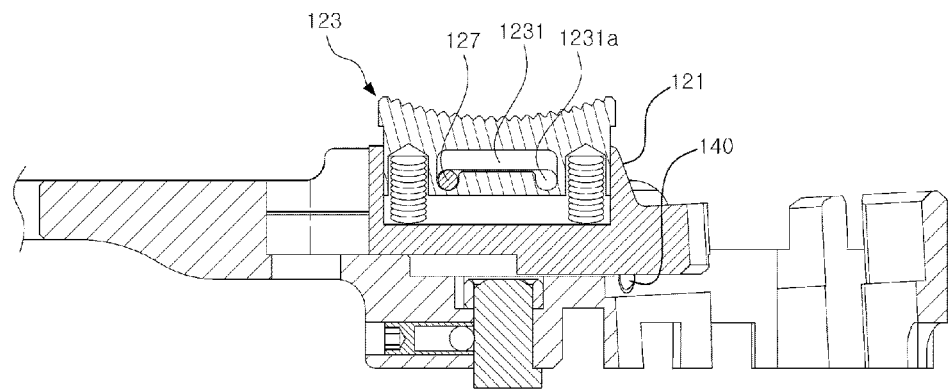
Figure 8:
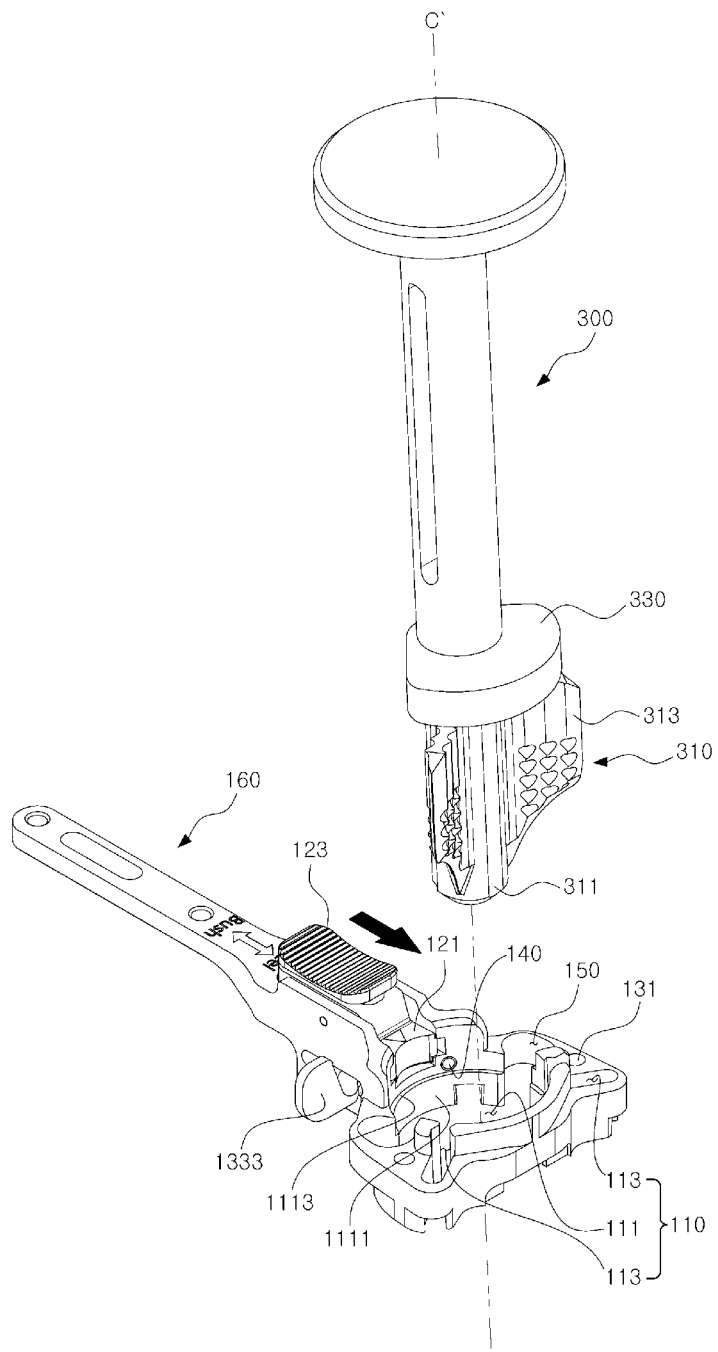
FIGS. 8 and 9 are perspective views of a state in which a keel punch is guided in the baseplate trial holding apparatus according to the embodiment of the present disclosure.
Figure 9:
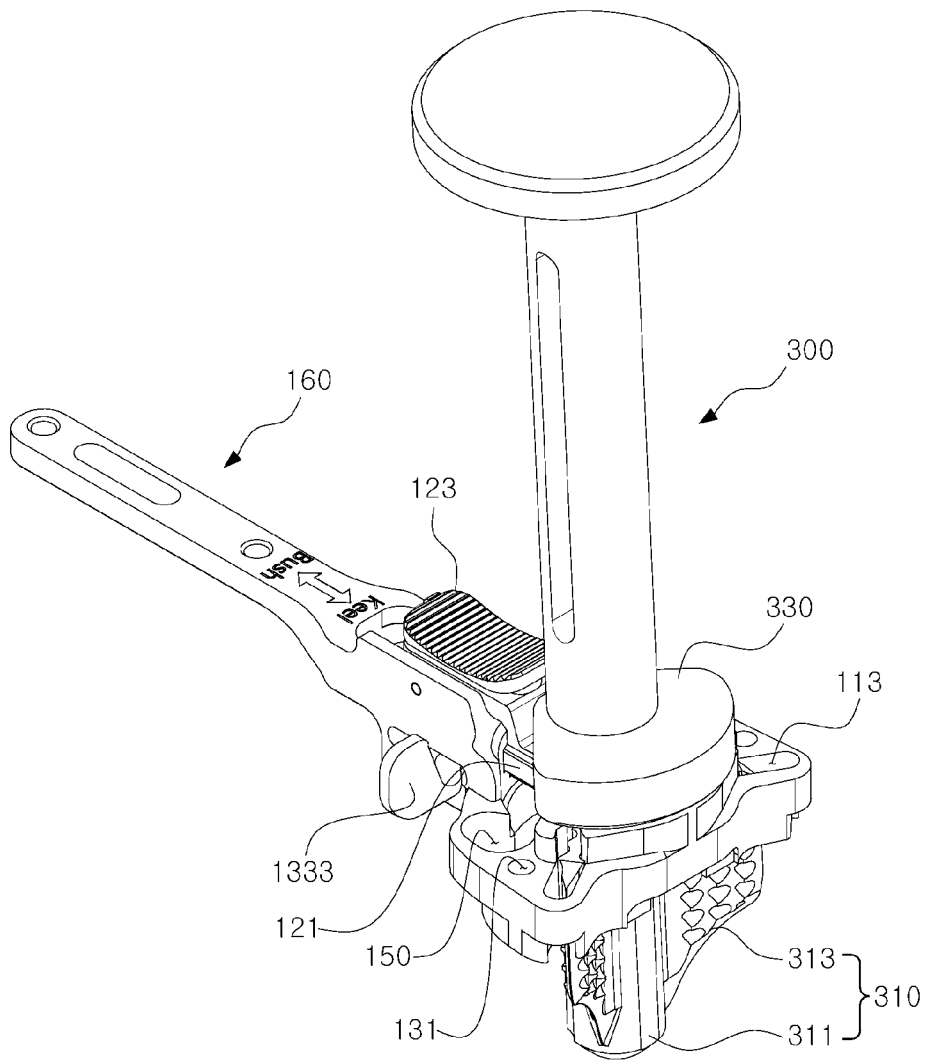

A detailed configuration and operation principle of the keel location fixing part 120 can be identified through FIGS. 6 and 7, the keel location fixing part 120 includes a stopper 121, a press switch 123, an elastic member 125, and a hooking member 127.

The stopper 121 has a form of being able to be fixed forward and fixed rearward, and is a portion that may be introduced into the central through portion 111 during the forward fixing to cause a hooking portion 320 protruding outwards to be hooked by an upper end of a keel 310 of the keel punch 300 when the keel punch 300 is inserted. The stopper 121 is not exposed to the interior of the central through portion 111 during the rearward fixing such that the offset bush guide 400, the drill guide 500, and the reamer guide 600 may be seated in the central through portion 111, and is brought into a state of being introduced into the central through portion 111 during the forward fixing to function to determine the insertion limit of the keel punch 300 when the keel punch 300 is inserted through the central through portion 111 and the guide slit 113. The stopper 121 includes an accommodation portion 1211 having an opened upper end, and a slot 1213 formed on the left and right side surfaces of the accommodation portion 1211 in the lengthwise thereof.

Meanwhile, because an end of the stopper 121, which is introduced into the central through portion 111, contacts the keel stem portion 311 of the keel punch 300 while having a shape that is complementary with the keel stem portion 311 of the keel punch 300 during the forward fixing, the stopper 121 can additionally guide the keel punch 300. That is, the stopper 121 can stably guide the keel stem portion 311 of the keel punch 300 regardless of the inner diameter of the central through portion 111. As a result, according to the present disclosure, even when the inner diameter of the central through portion 111 is larger than the outer diameter of the keel stem portion 311 of the keel punch 300, the keel stem portion 311 of the keel punch 300 can be guided, and accordingly, the entire keel punch 300 can be guided very precisely.

The press switch 123 is a configuration that functions to move the stopper 121 forwards and rearwards. A lower portion of the press switch 123 is accommodated in the accommodation portion 1211 formed at an upper end of the stopper 121. A lower portion of the press switch 123 accommodated in the accommodation portion 1211 includes a sliding groove 1231 that passes through left and right surfaces thereof, and has recesses 1231a and 1231b recessed downwards at opposite lengthwise ends thereof such that the lengthwise cross-section thereof has an inverse U shape.

The elastic member 125 is disposed between the stopper 121 and the press switch 123 to function to provide an elastic restoring force to the press switch 123 upwards and downwards. The elastic member 125 causes only the recesses 1231a and 1231b formed at opposite ends of the sliding groove 1231 to communicate with the slot 1213 when a downward force is not applied to the press switch 123, and causes the remaining portions of the sliding groove 1231, except for the recesses 1231a and 1231b, to communicate with the slot 1213 when a downward force is applied to the press switch 123.

The hooking member 127 is a portion that passes through the sliding groove 1231 of the press switch 123 and the slot 1213 of the stopper 121 such that opposite ends thereof is fixed to the baseplate trial holding apparatus 100. When a downward external force is not applied to the press switch 123 in a state in which the hooking member 127 is disposed to pass through the front recess 1231a of the sliding groove 1231 and the slot 1213 of the stopper 121, the stopper 121 maintains the rearward fixing state (a of FIG. 7). Further, if a downward external force is applied to the press switch 123 such that the remaining portions of the sliding groove 1231, except for the recesses 1231a and 1231b of the sliding groove 1231, communicate with the slot 1213 (b of FIG. 7) and the press switch 123 moves forward and the pressing state is released, the hooking member 127 is disposed to pass through the rear recess 1231b of the sliding groove 1231 and the slot 1213 of the stopper 121 so that the stopper 121 is forward-fixed and the stopper 121 maintains a state of being introduced into the central through portion 111 (c of FIG. 7).

The plate fixing part 130 is a part that is fastened to the baseplate trial 200. The plate fixing part 130 includes a boss insertion hole 131 and a locking unit 133.

The boss insertion hole 131 is a hole, into which a boss 231 protruding from the proximal surface 230 of the baseplate trial 200 is inserted when the boss insertion hole 131 is coupled to the baseplate trial 200. The boss insertion hole 131 is formed at a location corresponding to the location of the boss 231 when the baseplate trial holding apparatus 100 is coupled to the baseplate trial 200, and causes the baseplate trial holding apparatus 100 and the baseplate trial 200 to secure precise coupling locations.

The locking unit 133 is a part that causes the baseplate trial 200 to be coupled tightly as the locking unit 133 is press-fitted with a coupling recess 271 formed in the baseplate trial 200 when being coupled to the baseplate trial 200. The locking unit 133 includes a latch 1331 press-fitted with the coupling recess 271 and a rotation switch 1333 that causes the latch 1331 to be rotated with reference to a shaft formed vertically.

The latch 1331 is moved by the rotation switch 1333, and if the rotation switch 1333 is pushed forwards, the baseplate trial holding apparatus 100 and the baseplate trial 200 are adhered to each other while the latch 1331 is press-fitted with the coupling recess 271.

Before the press-fitting of the latch 1331, the baseplate trial holding apparatus 100 and the baseplate trial 200 has a gap by which they move horizontally to a degree with respect to each other in a state in which they overlap each other, and the baseplate trial holding apparatus 100 cannot hold the baseplate trial 200 in the original direction. As the latch 1331 is press-fitted with the coupling recess 271 in this state, the baseplate trial holding apparatus 100 and the baseplate trial 200 are adhered to each other, and the baseplate trial 200 cannot move upwards and downwards. As a result, the baseplate trial holding apparatus 100 and the baseplate trial 200 can be stably coupled to each other.

The indexing unit 140 is a part that protrudes from the inner wall of the central through portion 111 to be pressed by an external force and restored by elasticity. As described above, the central through portion 111 has a cylindrical shape, and the offset bush guide 400, the drill guide 500, and the reamer guide 600 may be seated in the central through portion 111.

The indexing unit 140 has indexing grooves 411 formed on an outer peripheral surface of the seating portion 410 in contact with the inner wall of the central through portion 111 at a predetermined interval, and allows rotation-stop type indexing of the offset bush guide 400 when being seated in the central through portion 111. In detail, the indexing unit 140 is realized by a ball plunger coupled to the inner wall of the central through portion 111 such that an end thereof including a ball may be exposed.

Figure 12:
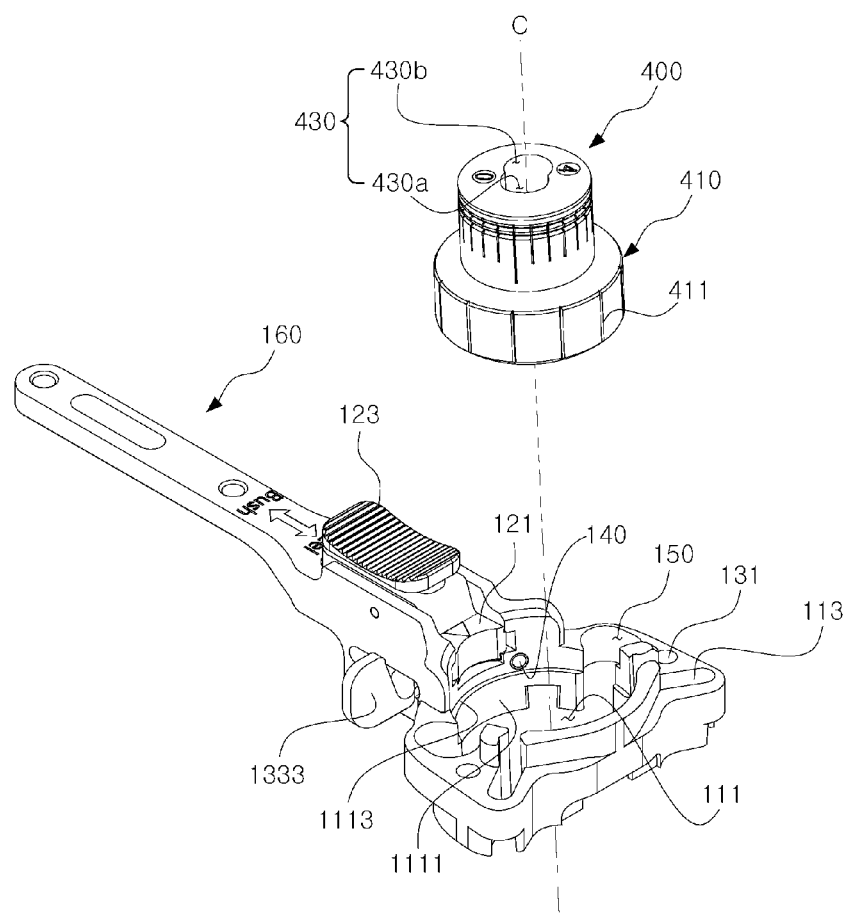
FIG. 12 is a perspective view of a state in which an offset bush guide is seated in the baseplate trial holding apparatus according to the embodiment of the present disclosure.
Figure 14:
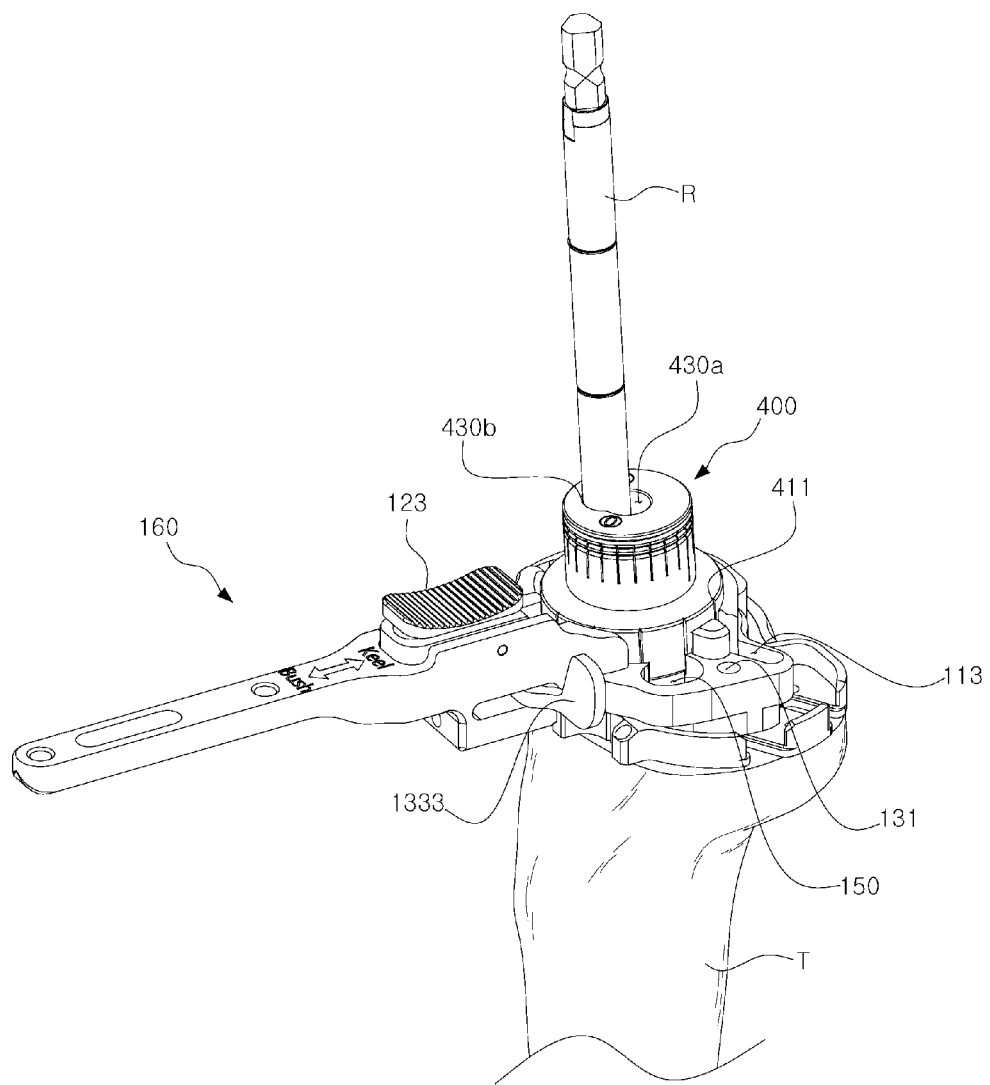
FIG. 14 is a perspective view of a use state of the offset bush guide seated in the baseplate trial holding apparatus according to the embodiment of the present disclosure.

Referring to FIGS. 12 and 14, the seating portion 410 of the offset bush guide 400 seated in the central through portion 111 has an outer diameter corresponding to the inner diameter of the central through portion 111. The offset bush guide 400 has indexing grooves 411 that are seated and inserted such that the outer surface of the seating portion 410 contacts the inner wall 1111 of the central through hole 111 while the center thereof coincides with the center c of the central through portion 111 and are formed on the outer surface of the seating portion 410 at a predetermined interval. Accordingly, when the offset bush guide 400 rotates, portions between the indexing grooves 411 press the indexing unit 140 while compressing the indexing unit 140, and because the compression forces of the indexing groove 411 are weak, the indexing unit 140 is restored by elasticity and is engaged with the indexing grooves 411 if the indexing grooves 411 and the indexing unit 140 meet each other in a process of rotating the offset bush guide 400. Accordingly, a stop feedback occurs.

Through the method, rotation-stop type indexing of the offset bush guide 400 is made. If the indexing grooves 411 are formed at an interval of 15° or 30°, rotation-stop feedbacks can be obtained at an interval of 15° or 30°.

As can be identified through FIG. 4, the pin insertion 150 is a part that is formed to communicate with the pin hole 290 formed in the baseplate trial 200 to secure an insertion space of the pin p for fixing the baseplate trial 200 to the tibia. A proper coupling location of the baseplate trial 200 is determined after being seamed with the proximal end of the tibia in a state in which the baseplate trial holding apparatus 100 and the baseplate trial 200 are coupled to each other in a surgical process of total knee arthroplasty or revision total knee arthroplasty, and when the proper coupling location is fixed, the pin p can be coupled to the pin hole 290 through the pin insertion part 150. The pin insertion part 150 is formed to be opened toward the outside of the central through portion 111, and in this way, due to the opened side, the pin p can be easily inserted.

The handle 160 is a part that is gripped by a doctor who performs a gripping surgery in a state in which the baseplate trial holding apparatus 100 holds the baseplate trial 200. In a state in which the baseplate trial 200 is coupled to the baseplate trial holding apparatus 100, a doctor who conducts a surgery through the handle 160 can properly determine a coupling location of the baseplate trial 200 on the tibia.

The handle 160 includes a through portion 161 formed vertically for insertion of an alignment rod. In detail, through holes 161a and 161c having an inner diameter corresponding to the outer diameter of the alignment rod are formed on the front and rear sides, respectively, and a slot hole 161b is formed between the through holes 161a and 161c. In this way, a plurality of through portions 161 are formed in various forms, and thus according to the present disclosure, the baseplate trial holding apparatus 100 can be usefully utilized in the alignment process.

Next, a knee joint implant surgical instrument set according to the present disclosure will be described.

The knee joint implant surgical instrument set according to an embodiment of the present disclosure includes the baseplate trial holding apparatus 100, the baseplate trial 200, the keel punch 300, the offset bush guide 400, the drill guide 500, and the reamer guide 600.

The baseplate trial holding apparatus 100 is as described above.

As described above, the baseplate trial 200 is a member that is temporarily coupled to the tibia to be used for performing operations, such as setting of a coupling location of a tibia implant, drilling, offsetting, and reaming, before the tibia implant is coupled to the tibia during total knee arthroplasty or revision total knee arthroplasty, and is disposed in the cut proximal tibia to be used. As illustrated in FIGS. 4 and 5, the baseplate trial 200 includes a window 210, a proximal surface 230, a side wall 250, a distal surface 270, and a pin hole 290.

The window 210 is a part which is disposed on the tibia proximal surface to expose the tibia, and includes a window central portion 211 that vertically passes through a central portion of the baseplate trial 200, and a window slit 213 that is opened on opposite sides of the window central portion 211 to communicate with the window central portion 211. In a state in which the baseplate trial 200 is coupled to the baseplate trial holding apparatus 100, the window central portion 211 communicates with the central through portion 111, and the window slit 213 communicates with the guide slit 113.

Figure 17:
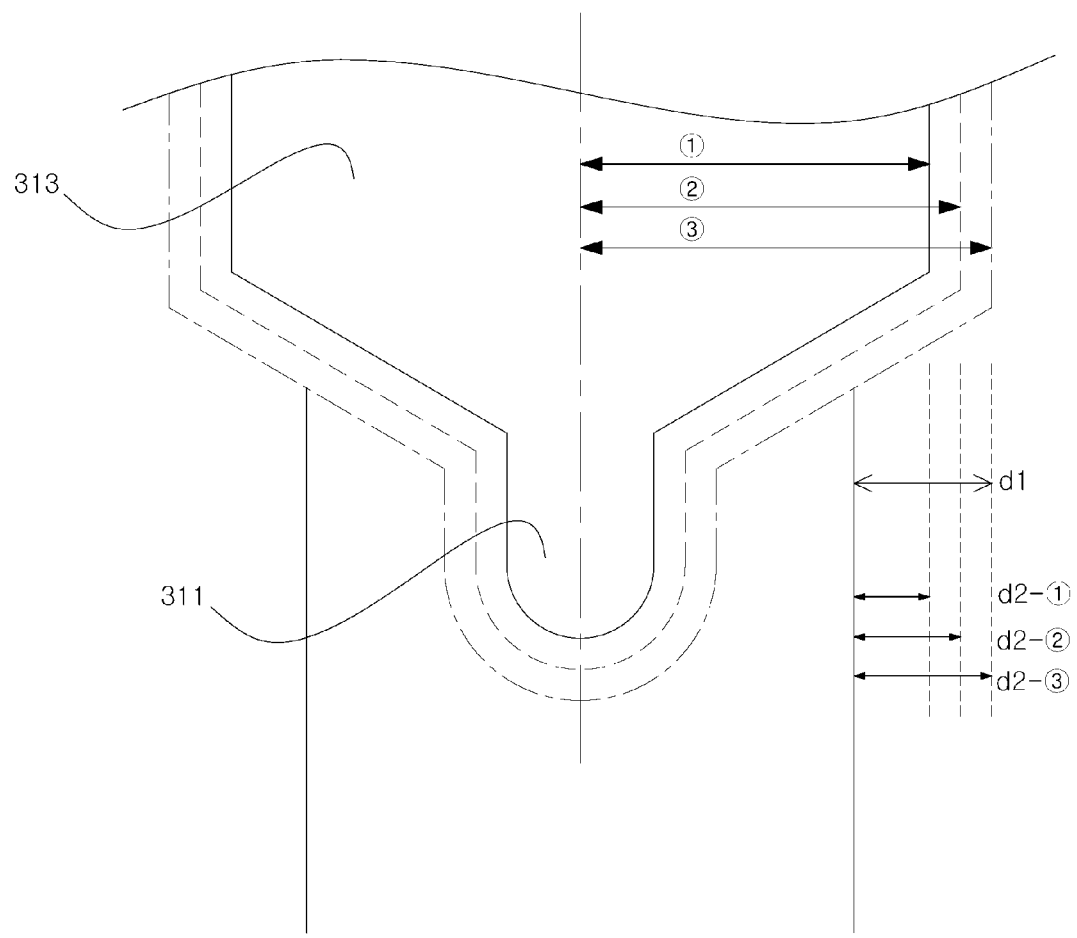
FIG. 17 is a conceptual view illustrating a correlation between a guide slit of the baseplate trial holding apparatus and a window slit of the baseplate trial in a knee joint implant surgical instrument set according to the embodiment of the present disclosure.

Referring to FIG. 17, a correlation between the window slit 213 and the guide slit 113 of the baseplate trial holding apparatus 100 can be identified. Here, d1 denotes the length of the guide slit 113, and d2-①, d2-②, and d2-③ denote the lengths of the window slits 213. The lengths d2-①, d2-②, and d2-③ of the window slit 213 may be equal to or smaller than the length d1 of the guide slit 113.

In the present disclosure, the baseplate trial 200 may have two or more sizes, and the width of the keel wing portion 313 of the keel punch 300 also may have two or more sizes according to the sizes of the baseplate trial 200. As a detailed example, when it is assumed that the baseplate trial 200 has five sizes (the smaller numbers mean the smaller sizes) of sizes, 3, 4, 5, 7, 9, and 11, the keel punch 300 has keel wing portions 313 having the widths ①, ②, and ③ of three sizes of a small size, a medium size, and a large size, the keel wing portion 313 of the small size ① is used in the baseplate trial 200 of size 3, the keel wing portion 313 of the medium size ② is used in the baseplate trials 200 of sizes 4, 5, 7, and 9, and the keel wing portion 313 of the large size ③ is used in the baseplate trial 200 of size 11. Then, as the window slit 213 of the baseplate trial 200 of size 3 has the length of d2-①, only the keel wing portion 313 having the width of the small size ① may pass, as the window slit 213 of the baseplate trial 200 of sizes 4, 5, 7, and 9 has the length of d2-②, the keel wing portion 313 having the width of the medium size ② may pass, and as the window slit 213 of the baseplate trial 200 of size 11 has the length of d2-③, only the keel wing portion 313 having the width of the large size ③ may pass. Through the configuration, an excessive keel cavity can be prevented from being generated due to the keel punch 300.

The proximal surface 230 is a part that constitutes an upper surface of the baseplate trial 200, and the baseplate trial holding apparatus 100 is seated on the proximal surface 230. The proximal surface 230 includes a boss 231 protrudes at a location corresponding to the location of the boss insertion hole 131 in the proximal direction when being coupled to the baseplate trial holding apparatus 100 to secure a precise coupling location.

The side wall 250 is a part that defines the outer shape of the proximal surface 230. The baseplate trial holding apparatus 100 is seated in the insertion space defined by the side wall 250 while overlapping the insertion space.

The distal surface 270 is a part that contacts the cutoff proximal end of the tibia. A coupling recess 271 is formed in the distal surface 270 in a form in which the locking unit 133 of the baseplate trial holding apparatus 100 is press-fitted with the coupling recess 271.

The pin hole 290 is a part, into which the pin p for fixing the baseplate trial 200 to the tibia is inserted, and communicates with the pin insertion part 150 of the baseplate trial holding apparatus 100.

As described above, the keel punch 300 is an apparatus that is inserted through the keel location setting part 110 of the baseplate trial holding apparatus 100 and the window 210 of the baseplate trial 200 to define the keel cavity in the tibia. As can be identified through FIGS. 8 to 11 and 17, the keel punch 300 includes a keel 310 and a hooking part 330.

The keel 310 is a part that defines a keel cavity in the tibia, and includes a keel stem portion 311 and a keel wing portion 313.

The keel stem portion 311 is a portion that constitutes the center of the keel 310 while having a cylindrical shape protruding in the distal direction.

The keel wing portions 313 are a pair of portions that extend in parallel to the side surfaces of the keel stem portion 311 while having an angle corresponding to the angle defined by the pair of guide slits 113 of the baseplate trial holding apparatus 100 with respect to the central through portion 111. The keel wing portions 313 have curves corresponding to the guide 113a of the guide slit 113 of the baseplate trial holding apparatus 100.

The keel wing portions 313 may be formed to have two or more wing widths, and the relationships between two of the wing widths of the keel wing portions 313, the size of the baseplate trial 200, and the length of the window slit 213 have been described in detail above.

The hooking part 330 is a part that protrudes from an upper end of the keel 310 to the outside. The hooking part 330 is hooked by the keel location fixing part 120 to function to restrict the insertion depth of the keel punch 300.

Figure 13:
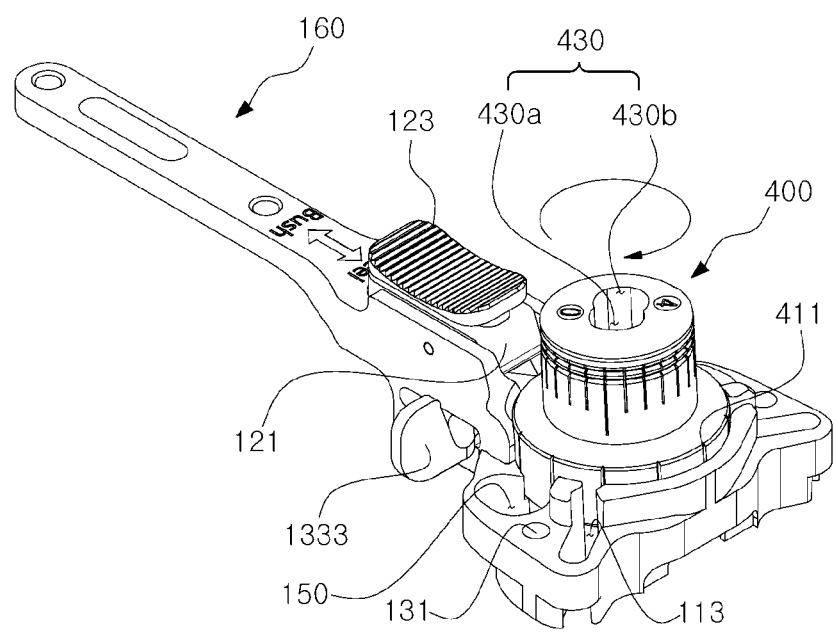
FIG. 13 is a perspective view of a state in which the offset bush guide seated in the baseplate trial holding apparatus according to the embodiment of the present disclosure is indexed in a rotation/stop scheme.

As illustrated in FIGS. 12 to 14, the offset bush guide 400 functions to perform reaming along a canal on the cut surface of the tibia T. Because the direction of the canal and the shape of the tibia T are different according to patients, offsetting is necessary, and the offsetting may be performed through the offset bush guide 400. The offset bush guide 400 has a form of being able to be seated in the central through portion 111 of the baseplate trial holding apparatus 100, and includes a seating portion 410 and a guide hole 430.

The seating portion 410 of the offset bush guide 400 is a part that is inserted into and seated in a seating space defined by the inner wall 1111 of the central through portion 111. The seating portion 410 of the offset bush guide 400 includes lengthwise indexing grooves 411 formed on the outer surface thereof at a predetermined interval and has a shape that may contact the inner wall 1111 while being hooked by the seating step 1113. The interactions of the indexing grooves 411 and the indexing unit 140 are as described above.

Two guide holes 430 of the offset bush guide 400 are portions that vertically pass through the offset bush guide 400 for insertion of rods R of the reamers, and the offset degree of the guide holes 430 are different at the centers thereof (430a and 430b). In a detailed embodiment, the offset distances from the centers from the two guide holes 430a and 430b may be 0 mm and 4 mm, respectively, and the offset distances from the centers may be 2 mm and 6 mm, respectively. When there is no offset in a state in which the shape of the baseplate trial 200 is seated on the cut surface of the tibia T, a portion of the rod R of the reamer is inserted into the guide hole having the offset distance of 0 mm, and if the sizes are not suitable otherwise, an optimum offset amount and an optimum offset direction are determined by using the guide holes having the offset distances of 2 mm, 4 mm, and 6 mm.

Figure 15:
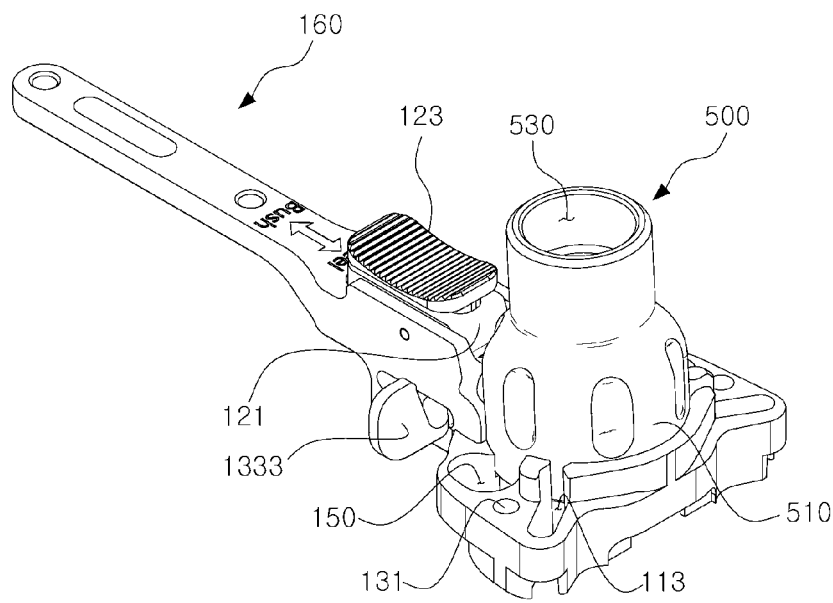
FIG. 15 is a perspective view of a state in which a drill guide is seated in the baseplate trial holding apparatus according to the embodiment of the present disclosure.

As illustrated in FIG. 15, the drill guide 500 is seated in the central through portion 111 of the baseplate trial holding apparatus 100 to function to guide the drill during a drilling operation through the cut surface of the tibia. The drill guide 500 includes a seating portion 510 and a guide hole 530.

The seating portion 510 of the drill guide 500 is formed at a lower portion of the drill guide 500 while having a shape that may be seated in the central through portion 111. In detail, the seating portion 510 is inserted into the seating space defined by the inner wall 1111 of the central through portion 111 and has a shape that may contact the inner wall 1111 while being hooked by the seating step 1113.

The guide holes 530 of the drill guide 500 are portions that pass upwards and downward for insertion and guide of the drill. The drill is inserted through the guide hole 530.

Figure 16:
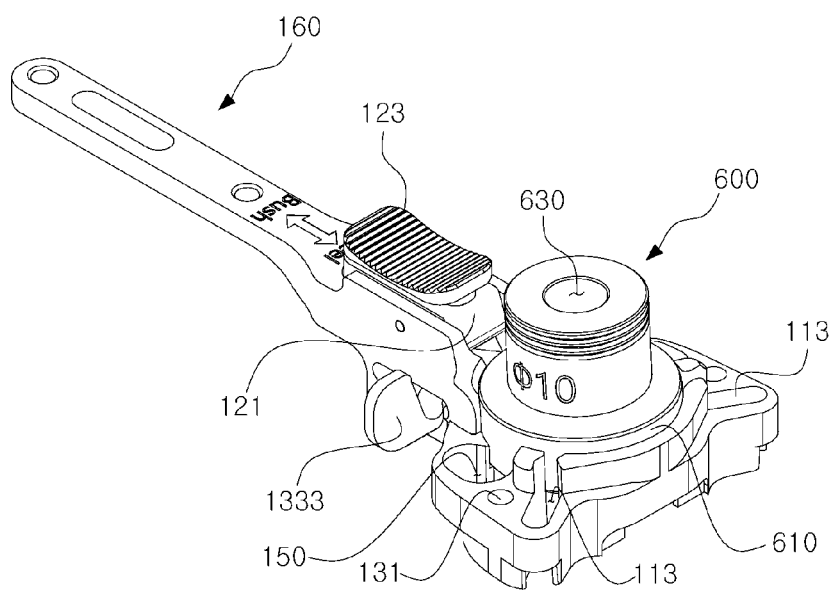
FIG. 16 is a perspective view of a state in which a reamer guide is seated in the baseplate trial holding apparatus according to the embodiment of the present disclosure.

As illustrated in FIG. 16, the reamer guide 600 is seated in the central through portion 111 of the baseplate trial holding apparatus 100 to function to guide the reamer during a reaming operation through the cut surface of the tibia. The reamer guide 600 also includes a seating portion 610 and a guide hole 630.

The seating portion 610 of the reamer guide 600 is formed at a lower portion of the reamer guide 600 while having a shape that may be seated in the central through portion 111. In detail, the seating portion 510 is inserted into the seating space defined by the inner wall 1111 of the central through portion 111 and has a shape that may contact the inner wall 1111 while being hooked by the seating step 1113.

The guide holes 630 of the reamer guide 600 are portions that pass upwards and downward for insertion and guide of the reamer. The reamer is inserted through the guide hole 630.

Although various embodiments of the present disclosure have been described until now, it should be construed that the embodiments are simply embodiments for realizing the technical spirit of the present disclosure, and any modifications or corrections for realizing the technical spirit of the present disclosure fall within the scope of the present disclosure.

What is claimed is:

1. A baseplate trial holding apparatus which holds a baseplate trial disposed in a proximal tibia during total knee arthroplasty or revision total knee arthroplasty, the baseplate trial holding apparatus comprising:
   a keel location setting part configured to set an insertion location of a keel punch, the keel location setting part defining:
      a central through portion, through which a keel stem portion of the keel punch passes; and
      a guide slit configured to guide insertion of a keel wing portion of the keel punch; and
   a keel location fixing part configured to determine an insertion limit of the keel punch, wherein the keel location fixing part comprises a stopper configured to be displaceable between a fixed forward position and a fixed rearward position;
   wherein in said fixed forward position the stopper projects into the central through portion such that an upper end of a keel of the keel punch is hooked by the stopper when the keel punch is inserted into the central through portion.

2. The baseplate trial holding apparatus of claim 1, wherein the guide slit comprises a guide corresponding to a curve profile of the keel wing portion of the keel punch.

3. The baseplate trial holding apparatus of claim 2, wherein the guide comprises protrusions and recesses complementary to the curve profile of the keel wing portion of the keel punch.

4. The baseplate trial holding apparatus of claim 2, wherein the guide slit extends from the central through portion, such that the guide slit is connected to and in communication with the central through portion.

5. The baseplate trial holding apparatus of claim 4, wherein the keel location setting part defines a pair of guide slits including the guide slit, each of said pair of guide slits extending from the central through portion and being symmetrical to each other, said pair of guide slits forming an angle of less than 180° with reference to a center axis of the central through portion.

6. The baseplate trial holding apparatus of claim 1, wherein the stopper comprises a first end forming a shape complementary to the keel stem portion of the keel punch, said first end projecting into the central through portion when the stopper is in the fixed forward position, such that said first end contacts the keel stem portion when the keel stem portion is inserted into the central through portion and guides the keel stem portion during said insertion.

7. The baseplate trial holding apparatus of claim 1, wherein the keel location setting part comprises an inner wall forming a seating step in the central through portion, said seating step configured for receiving any one of a drill guide, an offset bush guide, and a reamer guide inserted into the central through portion.

8. The baseplate trial holding apparatus of claim 7, wherein the seating step of the inner wall is configured to prevent movement of the drill guide, the offset bush guide, and the reamer guide in a horizontal plane defined by the seating step when received by the seating step.

9. The baseplate trial holding apparatus of claim 8, the baseplate trial holding apparatus further comprising an indexing unit protruding from the inner wall, said indexing unit being retractable against an elastic tension and configured to extend into indexing grooves formed on an outer surface of the offset bush guide, when inserted into the central through portion to perform rotation-stop type indexing of the offset bush guide,
wherein the central through portion has a cylindrical shape.

10. The baseplate trial holding apparatus of claim 1, further comprising:
a plate fixing part for coupling with the baseplate trial.

11. The baseplate trial holding apparatus of claim 10, wherein the plate fixing part defines
a boss insertion hole configured to receive a boss protruding from a proximal surface of the baseplate trial during coupling of the plate fixing part with the baseplate trial.

12. The baseplate trial holding apparatus of claim 11, wherein the plate fixing part further comprises:
a locking unit press-fitted with a coupling recess formed in the baseplate trial for coupling with the baseplate trial when being coupled to the baseplate trial.

13. The baseplate trial holding apparatus of claim 1, further comprising:
a pin insertion part formed to communicate with a pin hole formed in the baseplate trial to secure an insertion space of a pin for fixing the baseplate trial to a tibia.

14. A knee joint implant surgical instrument set comprising:
the baseplate trial holding apparatus of claim 1; and
a baseplate trial coupled to the baseplate trial holding apparatus.

15. The knee joint implant surgical instrument set of claim 14, wherein the baseplate trial defines
a window passing through the baseplate trial and exposing a proximal surface of a tibia, the window of the baseplate trial communicating with the keel location setting part of the baseplate trial holding apparatus.

16. The knee joint implant surgical instrument set of claim 15, wherein the window comprises:
a window central portion, through which a keel stem portion of the keel punch passes; and
a window slit extending from the window central portion, said window slit configured for receiving the keel wing portion of the keel punch.

17. The knee joint implant surgical instrument set of claim 16, wherein a length of the window slit is smaller than or equal to a length of the guide slit.

18. The knee joint implant surgical instrument set of claim 14, further comprising one or more of:
a drill guide having a form of being able to be seated in the central through portion of the baseplate trial holding apparatus,
an offset bush guide having a form of being able to be seated in the central through portion of the baseplate trial holding apparatus, and
a reamer guide having a form of being able to be seated in the central through portion of the baseplate trial holding apparatus.

19. The knee joint implant surgical instrument set of claim 18, wherein each of the drill guide, the offset bush guide, and the reamer guide comprises a seating portion, the seating portion and an inner wall of the keel location setting part together configured to prevent movement of the drill guide, the offset bush guide, and the reamer guide in a horizontal plane perpendicular to the inner wall when the drill guide, the offset bush guide, or the reamer guide is seated in the central through portion.

* * * * *